United States Patent [19]

Heidelbach

[11] Patent Number: 4,475,890

[45] Date of Patent: Oct. 9, 1984

[54] RETAINER ELEMENT FOR A DENTAL PROSTHESIS

[76] Inventor: Gerhard Heidelbach, Marktplatz 6, D-8700 Würzburg, Fed. Rep. of Germany

[21] Appl. No.: 379,862

[22] Filed: May 19, 1982

[51] Int. Cl.³ .............................................. A61C 8/00
[52] U.S. Cl. ..................................................... 433/173
[58] Field of Search .............................. 433/173, 174

[56] References Cited

U.S. PATENT DOCUMENTS

| | | | |
|---|---|---|---|
| 711,324 | 10/1902 | Lacy | 433/174 |
| 3,905,108 | 9/1975 | Weiss et al. | 455/173 |
| 4,304,553 | 12/1981 | Heimke | 433/173 |
| 4,382,791 | 10/1983 | Misch | 433/173 |

FOREIGN PATENT DOCUMENTS 628238 2/1982 Switzerland ......................... 433/173

OTHER PUBLICATIONS

"Intramusosil Implants" by Ronald Evasic in the Journal of Prosthetic Dentistry May 1983, vol. 49, No. 5.

Primary Examiner—Robert Peshock
Attorney, Agent, or Firm—Bacon & Thomas

[57] ABSTRACT

A retaining element is disclosed made from a single piece made of a substantially inelastic material having one end attached to a prosthesis and having the other end, with a thickened part and a shaft, releasably insertable into an artificial recess of the jawbone. The fastening end is equipped with a threaded portion so that the retainer may be screwed into the prosthesis to a greater or lesser extent. The invention further concerns a prosthesis equipped in this manner and drills for the production of the artificial recess.

15 Claims, 38 Drawing Figures

Fig. 5b
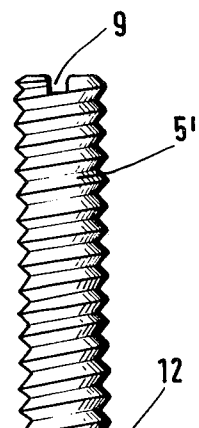
Fig. 5
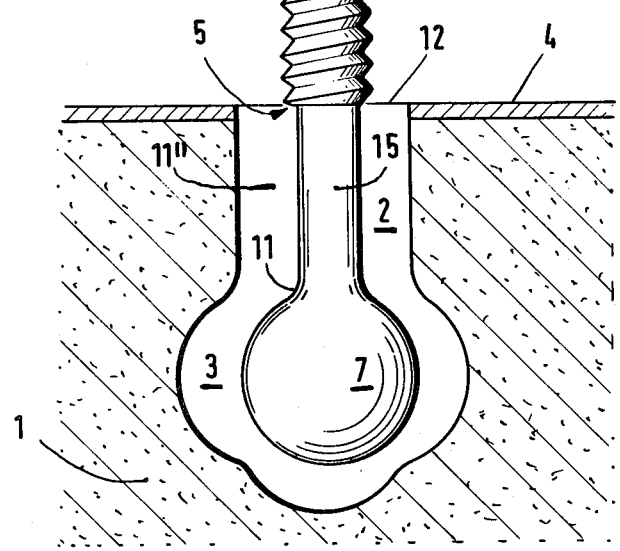
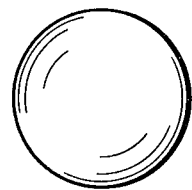
Fig. 5a

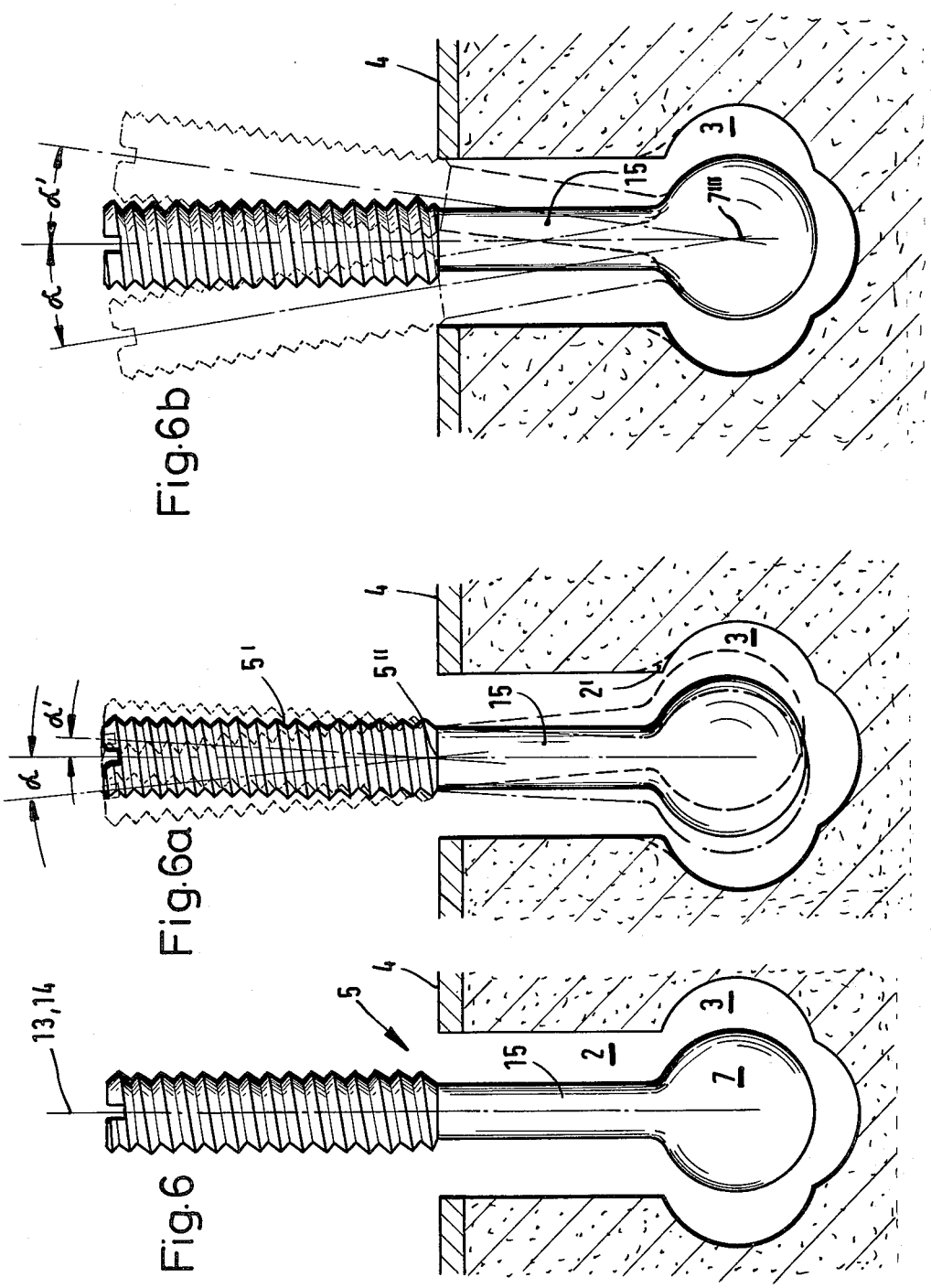

RETAINER ELEMENT FOR A DENTAL PROSTHESIS

BACKGROUND OF THE INVENTION

The invention relates to a retainer element (implant) for a dental prosthesis that is releasably insertable in an artificial recess of the jawbone. Typically, such a retainer element is provided at one end with an enlarged thickened part which fits into a recess in the jawbone and the other end of the retainer element (to be fastened in the prosthesis) has an undercut extending from the thickened part over the essential length of the retainer element. A retainer element of this type is shown in DE-OS No. 25 02 036. It consists of an elastic, hollow fastening end, a hollow shaft joined to said fastening end and to a thickened part, (also hollow and elastic) that is introduced in the recess in the bone. The fastening end is compressed by the application of an external pressure and the thickened part expanded with the aid of a medium, so that it will be held in the bone recess. These retainers are highly complex, excessively costly to manufacture and in practice much too susceptible to failure. As the result, they cannot be used with great success. The similarly complex actuating mechanism provided for the compression of the fastening end in the aforecited reference may be operated by the person wearing the prosthesis only with much difficulty or not at all; and, is not hygienic, as food particles may lodge in it. A further disadvantage consists of the fact that the retainer elements protruding from the prosthesis and the recesses in the jawbone must be parallel to each other, to make it possible for the patient to apply, wear and remove the prosthesis without pain. However, for anatomical and medical reasons, the dentist is unable to drill the recesses intended for the reception of the implants (retainer elements) into the jawbone in an exactly perpendicular manner and parallel to each other.

Further possible implantation methods are known besides the aforementioned retainer elements, for example, the subperiostal skeleton implantation. However, the surgical effort required is extraordinarily high and expensive.

SUMMARY OF THE INVENTION

It is the object of this invention to provide a relatively simple means, that requires less work by the dentist and provides a secure hold of the prosthesis in the jawbone, particularly in an atrophied jawbone. This invention also provides a holding retainer that is easily insertable and removable by the person wearing it. The invention is intended especially for a prostheses on the lower jaw. In the past such prosthesis could not be held in the mandible at all, or only with a great effort involving implants due to mandible shrinkage.

In order to achieve the objectives, the invention is initially characterized in that the retainer element, including its thickened part and its fastening end to be anchored in the prosthesis, consists of a solid, substantially inelastic material; and that said fastening end is provided with threads and has a recess on its frontal end for the introduction of a tool effecting the rotation of the retainer element, so that with access through a prosthesis orifice, an adjustment in height of the retainer element in the prosthesis is possible. This results in the following advantages: the retainer elements are single piece, solid bodies that may be produced at a substantially lower cost than the retainer elements according to DE-OS No. 25 02 036. Also, retainer elements according to the invention are strong and cannot easily be damaged.

To remove and insert a prosthesis equipped with the retainer elements according to the invention, it is necessary only to grip the prosthesis. It may therefore be equipped with the necessary number, even a larger number of retainer elements. Thus, a lower jaw prosthesis may be equipped, for example, with 15 retainer elements. Because of their configuration and mechanical strength, it is not necessary to place the axes of the retainer elements exactly parallel to the longitudinal axes of the recesses in the jawbone accepting them. This is of great importance in actual practice, as for the abovementioned reasons it is not possible to drill the recesses in the jawbone exactly parallel to each other. The dimensions of the thickened part of the retainer element located in the opening of the jawbone is always the same in the invention, while in the case of DE-OS No. 25 02 036, they are variable as the consequence of manufacturing inaccuracies and the unequal compression of the upper fastening end. The secure hold of the prosthesis is thereby endangered. The risk of a loosening of the lower thickened end from the shaft, which may occur with DE-OS No. 25 02 036, is eliminated by this invention. The threaded portion (with the recess to insert a tool) permits the length of the active part of the retainer protruding from the prosthesis to be varied, while preserving the single piece configuration of the retainer element, and its secure hold in the prosthesis. Depending on the size of this protruding part of the retainer, the retaining force acting on the retainer element, in the case of a given opening, becomes larger or smaller.

The artificial recesses or openings in the bone, may be prepared by the dentist by means of specially developed drills (to be discussed hereinafter) in a relatively simple manner. In the drilled out bone, a mucous membrane connective tissue layer forms, filling the space between the undercut portion of the implant and the remaining bone wall. As mentioned hereinabove, this provides a sufficient and also elastic retention of the retainer element implanted within the mandible. Following the abovedescribed extraction of the prosthesis and its retainer element for the purpose of cleaning, repairs or the like, from the mandible, reinsertion should be effected as soon as possible, because the mucous membrane tends to close the place of insertion of the implant rapidly, in the manner of the healing of a wound.

The abovementioned undercut not only effects the retention already described, but also allows the angular position of the drill channel to deviate from that of other drill channels. Since the undercuts extending over the length of the part of the retainer element located in the bone and the mucous membrane, the longitudinal axis of the retainer element may be inserted at a certain angle to the longitudinal axis of the associated drill channel in the bone. This angle may amount, for example, to ±12.5°, so that a total deviation is possible within a cone, the opposing lateral edges whereof have an included angle of approximately 25°. The invention, however, is not restricted to the abovecited angular measure.

According to a preferred embodiment of the invention, a shaft containing the undercut is provided, the diameter of the shaft expanding from the thickened part in the direction toward the end of the retainer element to be fastened in the prosthesis, in a conical manner, to the approximate diameter of the thickened portion. The thickest mucous membrane connective tissue is thereby formed immediately behind the thickened portion to provide adequate retention. However, at the upper end of the channel drilled in the bone and especially within the mucous membrane connective tissue the opening in the membrane formed by the conical shaft of the retainer element is approximately as thick as the thickened part and is maintained in the open state, while the prosthesis is in use. Consequently, the mucous membrane connective tissue must be squeezed very little during the removal and particularly during the insertion of the implant. There is, therefore, little pain to the patient during the removal and reinsertion of the implants. The cone of the shaft forms the above-mentioned angle of, for example, 25° by the principle of undercutting, so that in this embodiment it is not only possible to insert the implants vertically, but also when the angular deviations of the implants from the existing drill channels are within a certain range.

According to a further form of embodiment of the invention, the shaft equipped with the undercut may also be cylindrical, with its diameter equal to the undercut. The retention effect per implant obtainable with the embodiment is larger than in the case of the aforedescribed conical form, since a hollow cylindrical mucous membrane connective tissue of corresponding thickness is formed practically over the entire length of the shaft. The resistance of said connective tissue during the removal of the implant is correspondingly greater than in the case of the aforedescribed conical configuration, wherein a similar thick tissue layer is formed only immediately behind the thickening. It should be noted in connection with the form of embodiment having the cylindrical shaft, however, that said shaft holds the inlet and outlet orifice of the implant open in the area of the mucous membrane connective tissue covering the bone only by its diameter and not by the diameter of the thickened part. This renders the insertion and removal of the implant somewhat more difficult and more painful for the patient than in the case of the aforedescribed conical configuration of the shaft. The principle of the invention is not abandoned by using a shaft configuration other than conical or cylindrical, as long as an undercut permitting the formation of connective tissue holding the implant, but permitting the insertion and removal of the implant, is provided.

The invention further includes the use of one or several retainer elements according to the invention, i.e., the protection of a prosthesis equipped with the aforesaid retainer elements. The invention concerns still further conical trepanning drill and drills with a spherical cutter as the active part of the drill and a subsequent shaft of smaller diameter for the drilling of bone openings to receive the retainer elements according to the invention.

Further advantages and characteristics of both the retainer element (implant), and of the prosthesis and the drill will become apparent from the dependent claims and the drawing of examples of embodiment of the invention, attached hereto.

BRIEF DESCRIPTION OF THE DRAWINGS

Figures 1a and 1b show the corresponding bottom view and top view, respectively;

FIG. 5 shows a second embodiment of a retainer according to the invention in a lateral elevation;

FIGS. 5a and 5b show the bottom and top views corresponding to FIG. 5, 5a, 5b;

FIGS. 6, 6a and 6b show different angular positions of the embodiment of FIG. 5;

DETAILED DESCRIPTION OF THE PREFERRED EMBODIMENTS

Figure 1:
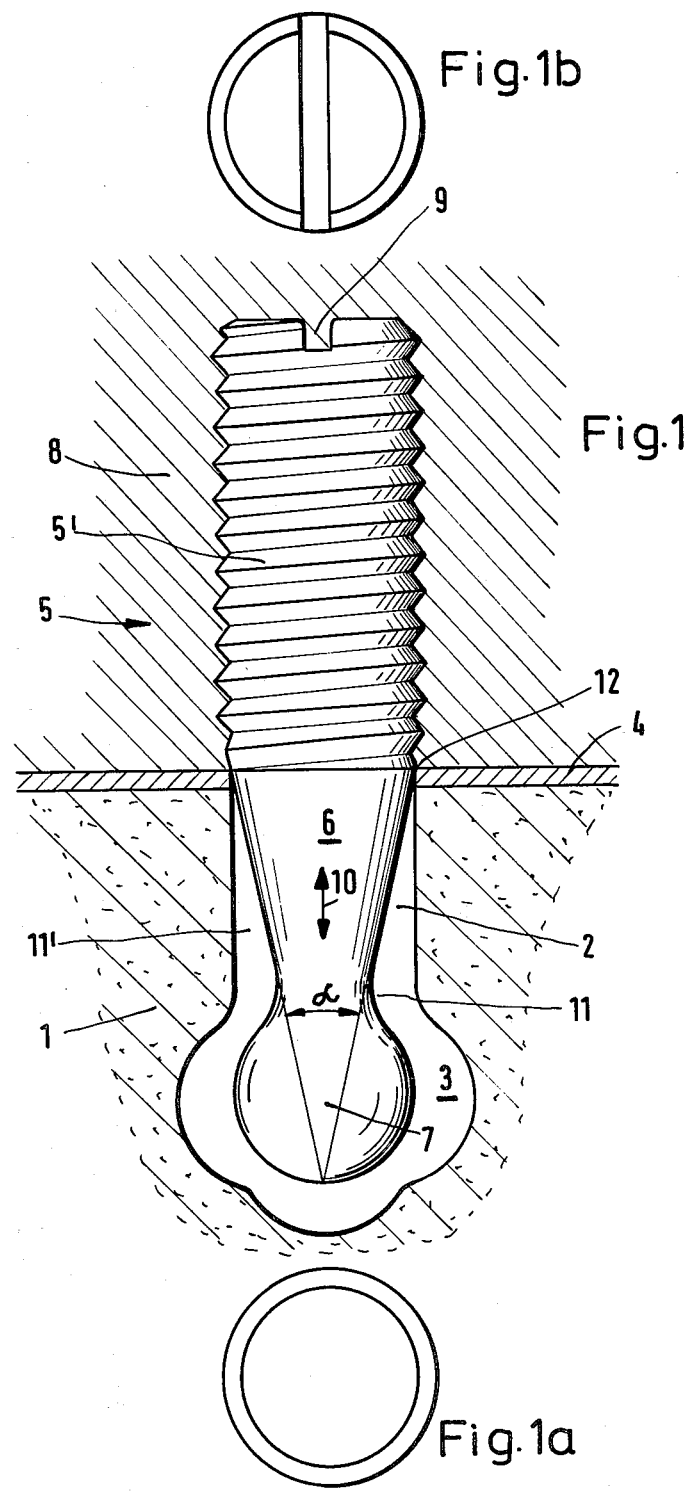
FIG. 1 shows a first embodiment of a retainer according to the invention in a lateral elevation.

With a drill (possible embodiments of which are shown and described in FIGS. 27 to 31), in the spongy, porous bone 1, preferably of the mandible, a channel 2 is drilled for each retaining position, said channel preferably ending in an expansion 3. The symbol 1' designates the hard bone, which for graphical reasons is numbered in FIG. 2 only and is represented further in FIG. 3a. The mucous membrane surrounding the bone is designated 4. A retainer element 5 is inserted in this artifically prepared wound of the jawbone as the implant; it shall be described in detail hereinafter.

In the embodiment of FIGS. 1 to 4, the retainer element 5 has a threaded body 5' with a diameter of for example 3.5 mm and a length of 7.5 mm. This threaded body is followed for the forming of the undercut by a conical shaft 6, ending in a thickened portion 7, which is spherical in this instance. The diameter of the conical shaft 6 at the transition into the threaded body 5' is 3.0 mm in this example and at the transition to the thickened part or head 7, 1.5 mm, with a shaft length of 4.0 mm. The cone angle 2 then is $\alpha = 25°$. The diameter of the thickened part 7 is 3.0 mm, thus corresponding to the diameter of the cone shaft at the transition to the threaded body 5'. This angle is recommended in the case of the dimensions of the implants according to the examples and the dimensions of the corresponding drill according to FIGS. 27 to 31. It should be understood that the abovecited angular and dimensional data are examples only and that the invention is not restricted to them. The same is true for dimensions given in subsequent embodiments.

The threaded body 5' is secured in the prosthesis body 8, and is preferably cast around with the material of the prosthesis body, (usually consisting of a synthetic plastic substance) so as to simultaneously form the internal threads of the prothesis conforming to the threads of the body 5'. The threaded body has a slot 9 for the insertion of a screwdriver in its surface on the side of mastication. The position of the implant may be adjusted thereby in the direction of the arrow 10, relative to the prosthesis. When the final position has been established, the frontal surface of the threaded body with the slot 9, may be cast with a synthetic plastic.

The artifically created wound or opening 2, 3 in the jawbone will be covered in the course of normal healing with a mucous membrane connective tissue, adhering very tightly to the implant inserted in the wound. As the result, the conical shaft 6, the thickened part 7 and the preferably arc shaped transition 11 (location of the largest undercut) are tightly covered by this secondary mucous membrane connective tissue holding the implant, thereby attaining the so-called retention effect.

The implant may be extracted from the mucous membrane connective tissue after the healing of the wound by overcoming the holding force of the mucous membrane connective tissue, or even prior to healing, wherein the mucous membrane connective tissue surrounding the transition location 11 must be compressed to the greatest extent since it offers the greatest resistance. It is an advantage of this embodiment with a conical shaft 6 that at the exit point 12, i.e., within the area of the primary mucous membrane covering the jawbone on top, the part of the conical shaft located there in the holding position, keeps the opening open, approximately equal to the diameter of the thickened part 7. As a result, during the extraction, the thick part 7 may pass through the opening almost without resistance and that further during the reinsertion the entry of the thick part 7 is effected without difficulty and in a practically painless manner. Furthermore, the thick part 7 slips relatively easily in the course of the reinsertion in the direction of insertion into the conically narrowing part of the layer of the mucous membrane connective tissue and then snaps into the holding position shown in FIG. 1, by overcoming the thickening of the connective tissue in the area of the undercut 11'.

Figure 2:
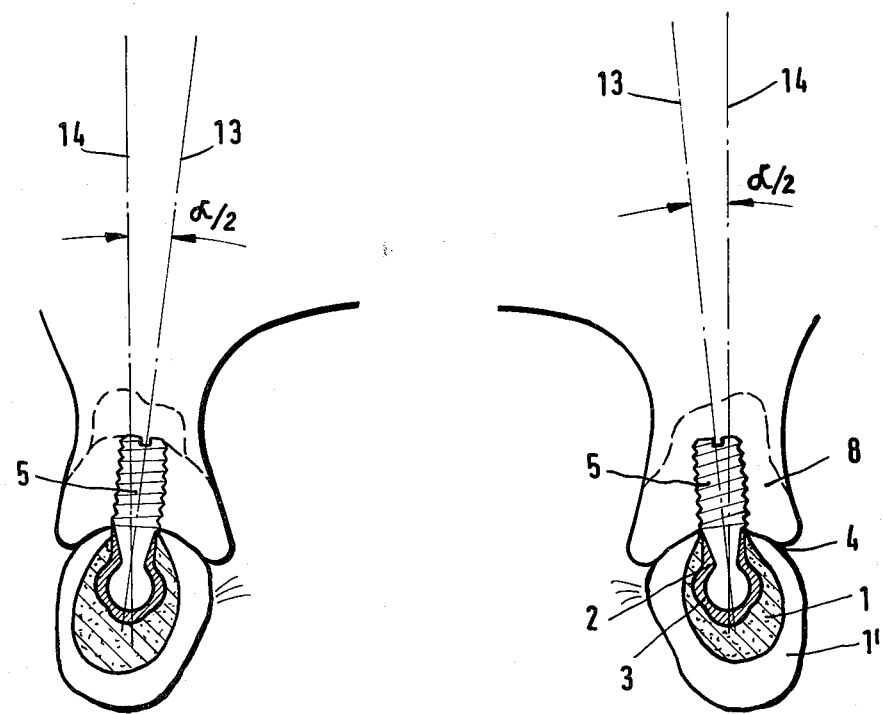
FIG. 2 shows a cross section through the molars (molar region) of the left and right mandible with the retainer element and the prosthesis according to the invention.
Figure 3:
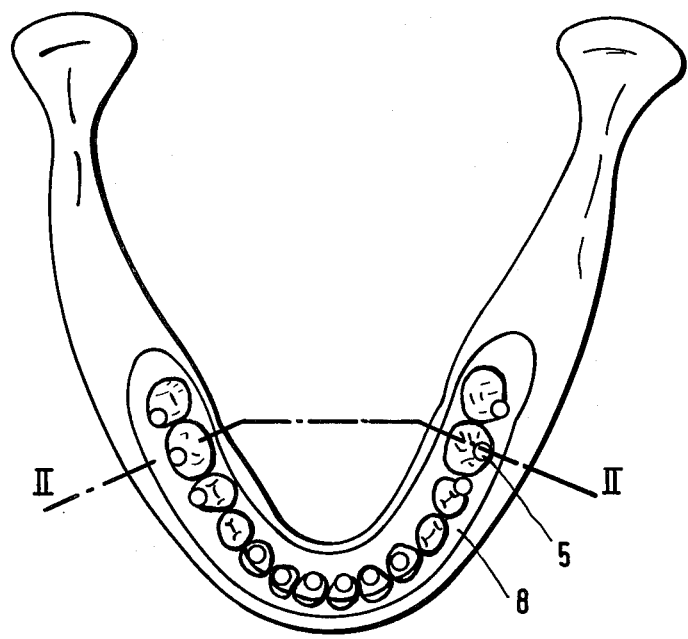
FIG. 3 shows a top view of a lower jaw with prosthesis and indicated retaining elements according to the invention.
Figure 3A:
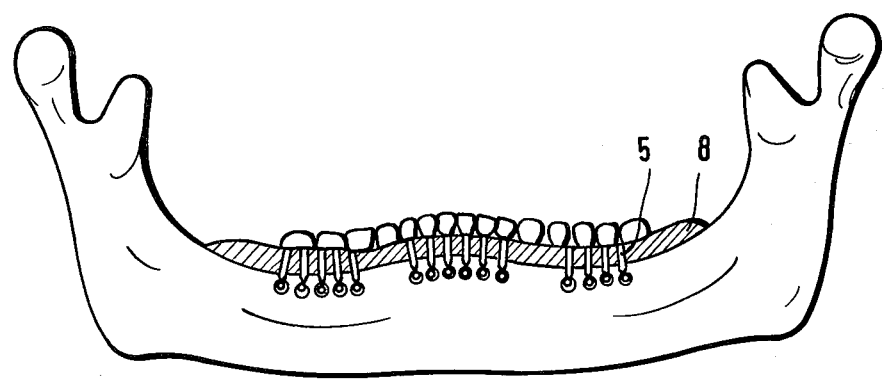
FIG. 3a shows a front elevation in the manner of an x-ray panorama image of FIG. 3.

FIG. 2 shows in a simplified manner a section through the mandible on the line II—II in FIG. 3 with two implants and the prosthesis, while illustrating further the fact that the longitudinal center axis 13 of the implants may include an angle $\alpha/2$ to the vertical 14 through the plane formed by the prosthesis. The angle $\alpha/2$ may amount to up to 12.5°, assuming the dimensions and angular data of the present embodiment. The implants may deviate from the direction in any way (rearwards, forwards, left or right). The longitudinal axes 13 of the implants of a prosthesis are thus not necessarily parallel to each other, rather the abovementioned angular deviations from the perpendicular and to each other, will be the rule.

FIG. 3 shows a top view, wherein the position of the implants and the retainer elements 5 are indicated by a point only.

Figure 4:
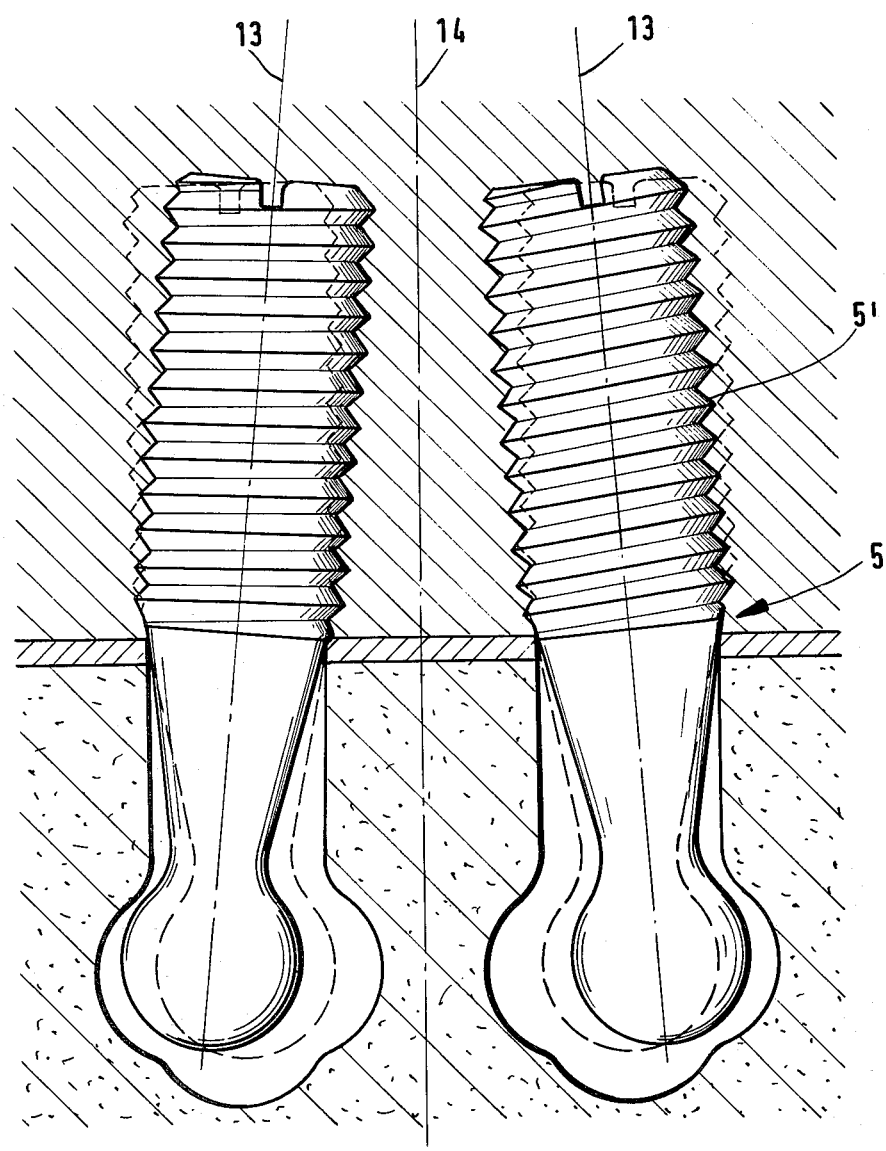
FIG. 4 shows a representation of the angular positions of the retainer elements with respect to the jaw.

FIG. 4 shows by means of the comparison of the position of two implants 5 with different angular settings of the axis 13, that the latter may deviate, for example, in the case of a total cone angle opening of $\alpha=25°$, from the perpendicular 14 by 12.5°, while still being insertable in the bore of the jawbone. In FIG. 4, the maximum angular deviation from the perpendicular is shown by solid lines, wherein the implant may still be extracted from the bore in the bone, while the broken lines show the position of the implant wherein its longitudinal axis 13 is parallel to the perpendicular 14. As mentioned hereinabove, the angular deviations may occur not only in the plane of drawing of FIG. 4, but in any other direction.

The embodiment shown in FIGS. 5 and 6 differs from that of FIGS. 1 to 4 in that the conical shaft 6 is replaced by the cylindrical shaft 15. The latter passes into the threaded body 5', which is correspondingly thinner than the threaded body of the preceding embodiment, while being retained in a similar manner in the body of the prosthesis, not shown, (symbol 8) and being adjustable by means of the threads. In this embodiment, the dimensions may be as follows: diameter of the threaded body 1.5 mm, length of the threaded body 6 mm diameter of the shaft 15, 1.0 mm, length of the shaft 15, 3.0 mm, while the spherical thickening 7 has a diameter of 3.0 mm. The transition 11 from the shaft 15 to the sphere 7 is again curved in the shape of an arc. The undercut, cylindrical in this case, is identified by 11''. For the rest, identical numbers are used for identical parts of the preceding embodiment. Here again, the artificially created wound in the jawbone is covered by a mucous membrane connective tissue, adhering both to the spherical head 7 and the implant shaft 15. In contrast to the embodiment with the conical shaft, in this case, by virtue of the implant shaft 15, which is thin over its entire length and the aforementioned cylindrical undercut 11'', a greater retention effect of the connective tissue is obtained, with the increase, in the case of the dimensions given for the two embodiments, amounting to approximately 50%. Since, in the area of the insertion and extraction opening 12, no opening corresponding to the diameter of the thick part 7 is maintained, both the extraction of the implant from the jawbone-connective tissue cushion and particularly the reinsertion is more difficult and more painful in comparison with the example with the conical shaft. This disadvantage must be balanced against the advantage of the higher retention effect and the implant must be dimensioned accordingly.

FIGS. 6 to 6b show that implants according to the embodiment of FIGS. 5 to 5b may also be pivoted with their longitudinal axis 13 by a total angular inclination of, for example 25°, or ±12.5° with respect to the perpendicular. The implants of this and of the other embodiment are solidly anchored in the prosthesis (however, they may be screwed in and out for adjustment) and may include with the vertical axis 14 of said prosthesis, along which they may be extracted from or inserted in said prosthesis, the abovementioned angle $\alpha$. The implants retained at this angle during the entire insertion or retraction process, without interfering with said insertion in or extraction from the bone. In FIG. 6, the axes 13, 14 are coinciding and the angle $\alpha$ is thus equal to zero. FIG. 6a shows the coincidence of the axes 13, 14 by solid lines according to FIG. 6 and with dotted and broken lines the angular deviations $\alpha$ and $\alpha'$, with the imaginary rotating point 5'' being located at the transition from the threaded part 5' to the shaft 15. It is further seen that in the realization of the bore in the bone, the edge 2' of transition of the bore 2 into the undercut 3 is being rounded off, as indicated by the broken line. Whenever the prosthesis is raised slightly, it is possible to move the prosthesis and the implants in a plane parallel to the mucous membrane 4. FIG. 6b again shows an implant according to FIGS. 5 to 5b in different angular positions $\alpha$ and $\alpha'$, wherein, however, the imaginary rotating point 7''' is now the center of the thickened part 7. With identical dimensions of the implants and the opening of the bore, the angular deviations $\alpha$, $\alpha'$ may be greater than in FIG. 6a.

The aforementioned advantage of the angular deviation of the axes 13 from the perpendicular 14 in each dimension is present in both embodiments from the undercut selected of the thickened part 7, wherein the shaft may be both conical or cylindrical or of any other configuration. However, in view of the easier insertion, the embodiment with the conical shaft is to be preferred. For this reason, the embodiments described in FIGS. 8 to 24 are preferably equipped with a conical shaft, although in principle the use of a cylindrical shaft is possible. It should be noted at this point that fundamentally each of the characteristics represented and described in each embodiment may be combined with the characteristics of another embodiment, to the extent that such a combination is technically feasible and rational.

Figure 7:
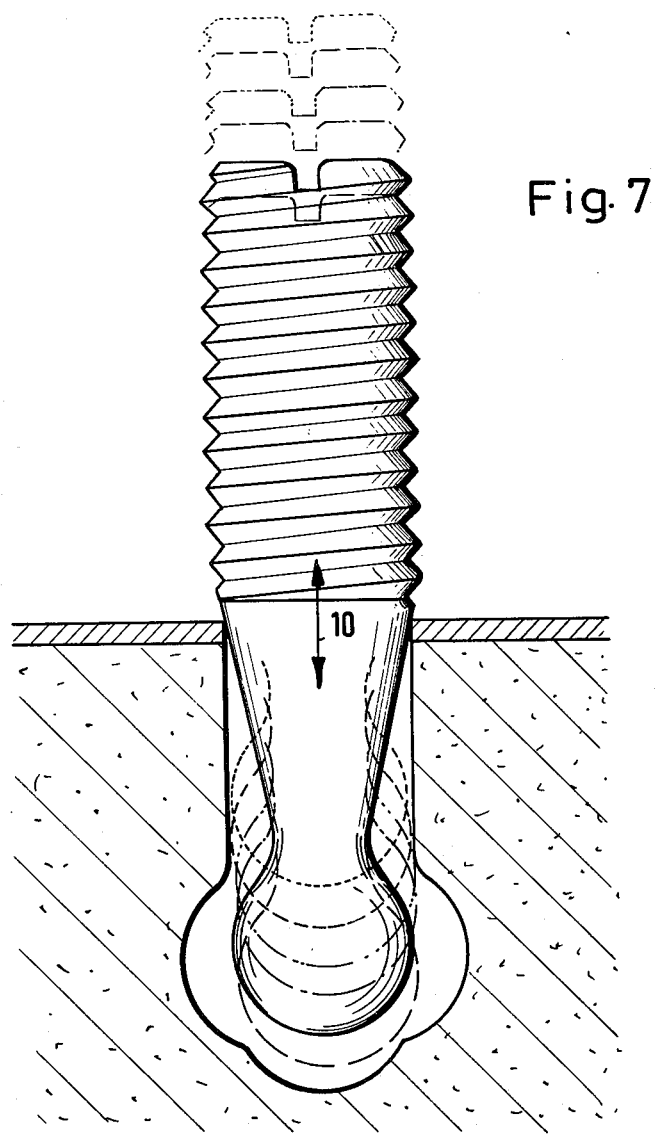
FIG. 7 shows the possible adjustment of the retainer element in the longitudinal direction in the embodiment of FIG. 1.
Figure 8:
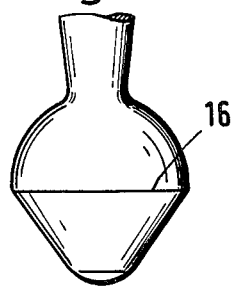
FIGS. 8 to 26 show a number of configurations of the thickened part of the retainer element.
Figure 9:
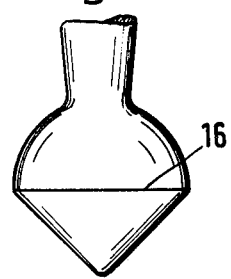
Figure 10:
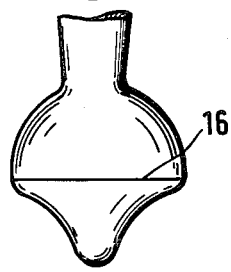
Figure 10A:
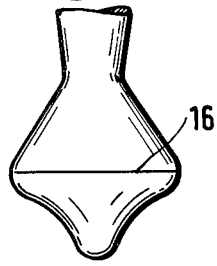
Figure 11:
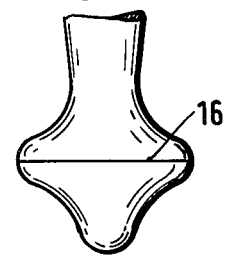
Figure 12:
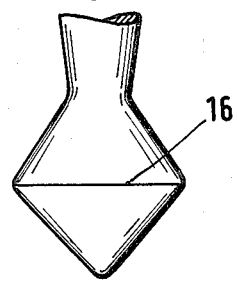
Figure 13:
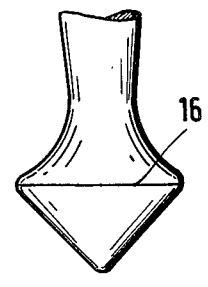
Figure 14:
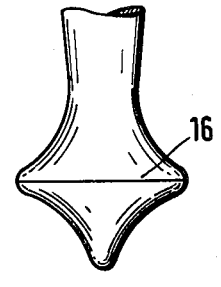

By means of the aforementioned adjustment of the implant relative to the prosthesis in the direction of the arrow 10, it is possible to adjust each individual implant of a prosthesis individually in its optimum position in view of increasing or decreasing the retention effect. FIG. 7 shows with the aid of an implant according to FIGS. 1 to 4, various possible adjustments by broken lines and the resulting changes in retention. In accordance with the foregoing, both the configuration of the shaft and of the thickened part may be different.

Figure 15:
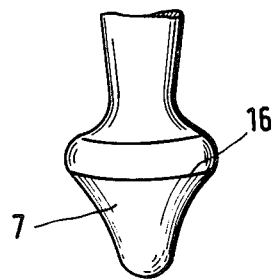
Figure 16:
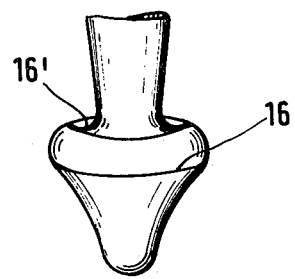
Figure 17:
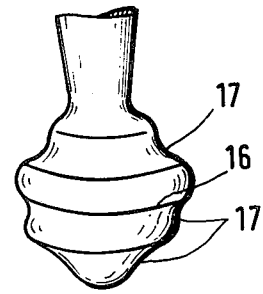
Figure 18:
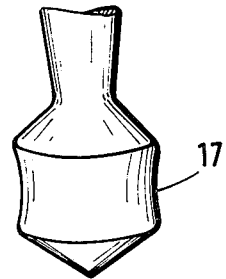

The description presented hereinabove already indicates that the form of the implant in combination with the form of the wound in the jawbone, determines the extent of the covering of the implant by the secondary mucous membrane and thus also the retention effect of the jawbone prosthesis. The different possibilities of the embodiment of the thickening shown in FIGS. 8 to 24 have on the one hand optimum retention effects as the result of the configuration of their halves located above the "equator" 16, i.e. their largest diameter, and facing the fastening ends 5. On the other hand, the tapering of the part of the thickening located below the "equator" 16 and facing away from the fastening end involved, provides as the result of the configuration selected, a relatively easy insertion of the implant in the jawbone. Attention is called in this context, as an example, to the downward tapering but still rounded form of the lower half of the thickened parts according to FIGS. 10 and 11. This is particularly apparent in the configuration of the thickening according to FIG. 15, which on the one hand greatly facilitates the insertion below the "equator" 16 by means of the relatively pointed shape, and on the other, presents an increased resistance to extraction by the surface extending almost at right angles to the direction of extraction, thereby realizing a correspondingly high retention effect. This retention is further reinforced in the example of embodiment of FIG. 16 by the flute 16' above the "equator" 16. The upper half of the thickened part facing the fastening end of the retainer element may thus possess a curvature which when viewed in the direction of the extraction, is concave (FIGS. 15 and 16). While in the examples of FIGS. 8 to 14, the so-called "equator", i.e., the largest diameter of the thickening is located in its center, it is shifted upward in the example of FIGS. 15, 16 and is located approximately at the transition from the center to the upper third of the thickening 7. This results (as demonstrated hereinafter) in an even easier insertion and in a retention that is enhanced even further. Furthermore, the mass of the retaining cushion formed is then equal in magnitude to the mass of the implant. In order to increase the retention effect, in the example of FIG. 17, the thickened part is provided with horizontal, circumferential grooves or recesses 17, which are penetrated by the layer of mucous membrane connective tissue. A similar configuration is shown in FIG. 18, with a surface 17' in the form of fluting.

Figure 19:
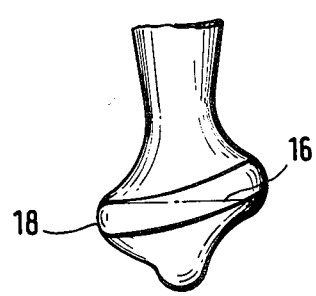
Figure 20:
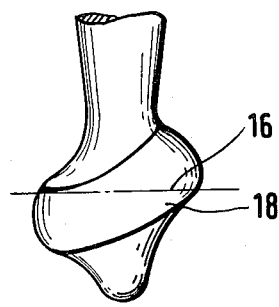
Figure 21:
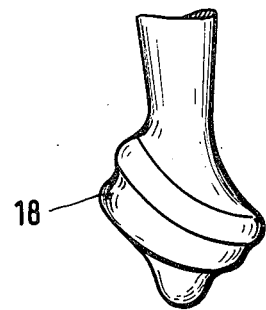
Figure 22:
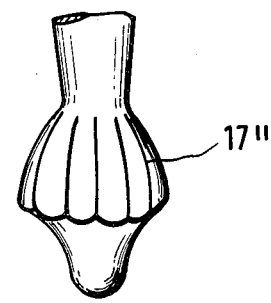

In each of the examples of FIGS. 19 to 21, a bead or thickening 18 is provided, extending at an angle of approximately 20°–45° to the plane of the "equator" 16. This further facilitates the insertion. Furthermore, a larger cushion of the mucous membrane connective tissue is formed and the retaining effect thereby reinforced. This facilitating of the insertion may also be effected by the curving of the half of the thickened part facing away from the fastening end of the retainer element, so that said half is protruding relatively far in this direction of insertion.

The configuration of FIG. 22 again yields an easier insertion and a more difficult extraction, with the vertical grooves 17'' provided in the upper half of the thickening 7 somewhat enhancing the retaining effect by presenting a larger area to the mucous membrane connective tissue. However, the retention effect is not as great as in the case of the grooves extending transverse to the direction of the extraction, for example, according to 17 and 17'.

Figure 23:
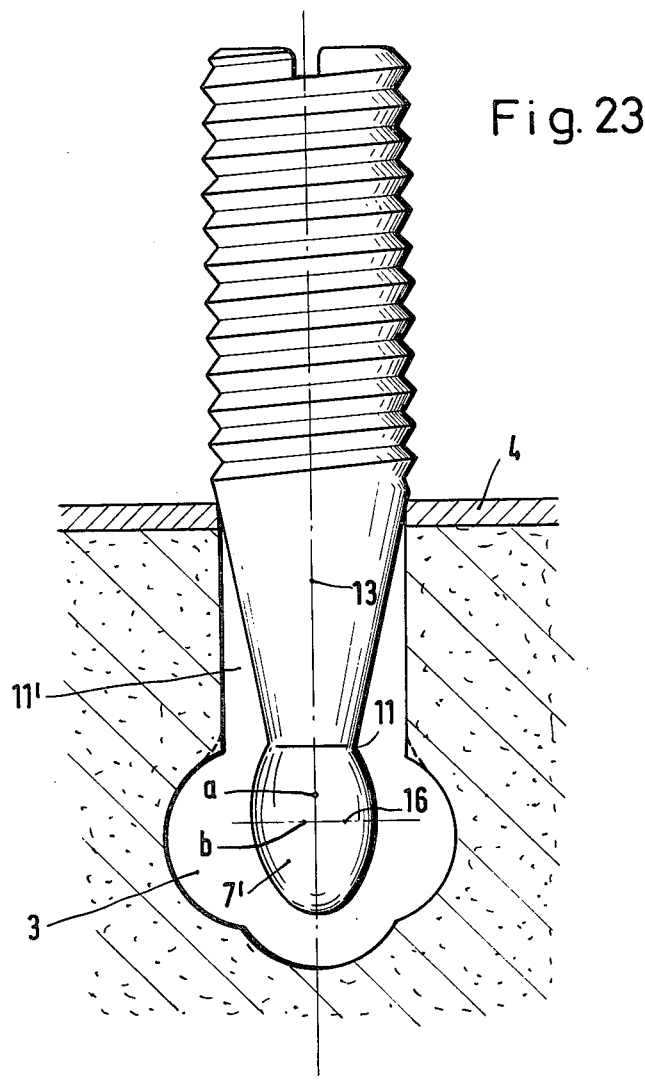

FIG. 23 shows a retainer element 5, wherein the thickened part 7' has the configuration of a rotational ellipsoid, with the long axis of the rotational ellipsoid coinciding with the longitudinal center axis 13 of the retainer element. The "equator" 16 of this rotational ellipsoid has the same position in height (relative to the longitudinal axis 13) as the equator of the spherical thickened part 7 according to the example of FIGS. 1 and 5. The length of the long axis a is equal to the diameter of the sphere forming the thickened part 7 in FIGS. 1 and 5. As, however, the short axis b of the rotational ellipsoid is correspondingly shorter than the diameter of the sphere 7 in FIGS. 1 and 5, both the inserting force and the retaining force here are correspondingly lower. The ellipsoid 7' necessarily displaces less of the connective tissue cushion 11' as the sphere 7 in the example of embodiment of FIGS. 1 and 5. The ellipsoidal thickened part 7', according to FIG. 23 may also be equipped with grooves, in particular transverse grooves, according to the aforedescribed embodiments.

Figure 24:
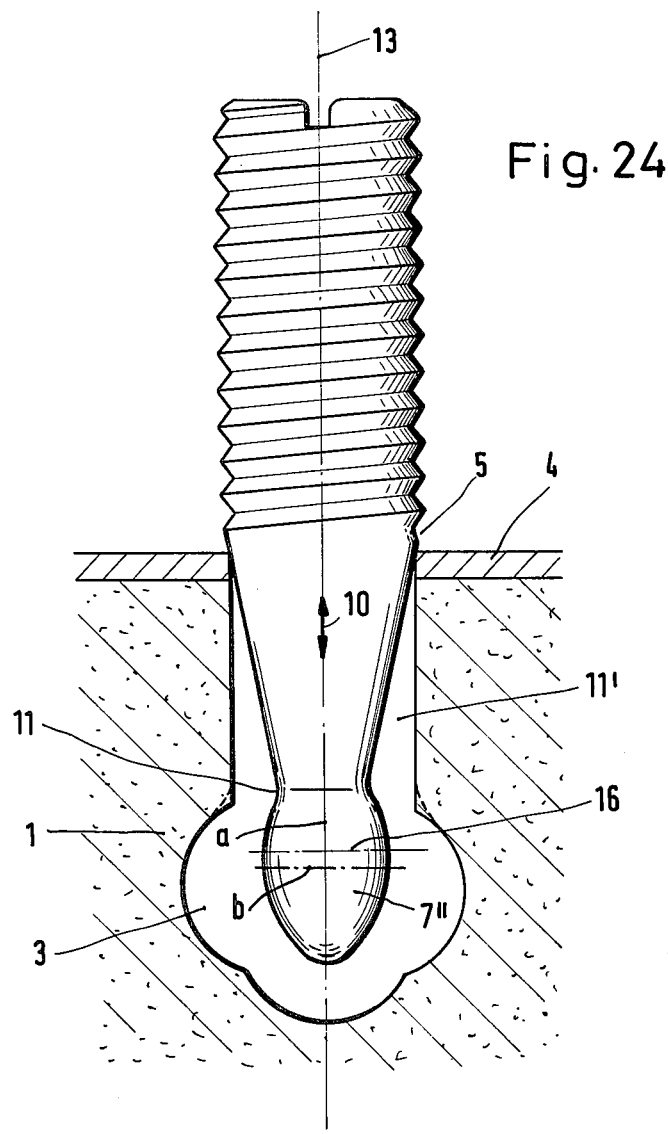

In the example of FIG. 24 the thickened part 7'' is egg shaped, with the tip of the egg being directed into the bore, so that the long axis a of the egg 7'' again coincides with the longitudinal axis 13 of the implant 5. The equator 16 is shifted slightly in the direction of the dental prosthesis. For the rest, the dimensions of the long (a) and the short (b) axes of the egg 7'' may be equal to the dimensions of the long axis a and the short axis b in the example of FIG. 23. The aforedescribed egg shape has the advantage that it offers greater resistance during extraction, while its resistance during insertion is lower (always relative to the a or b axis of a similarly dimensioned rotational ellipsoidal 7' and bone bores of equal size).

Figure 25:
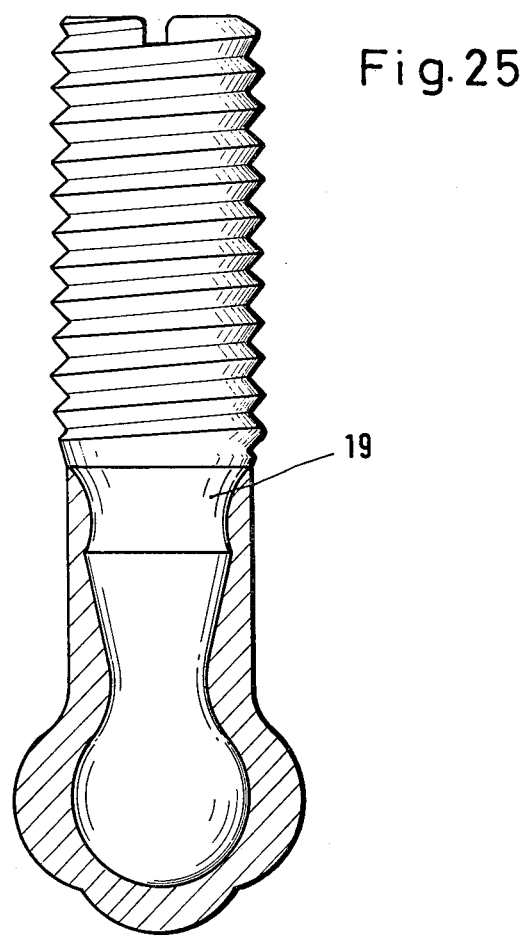
Figure 26:
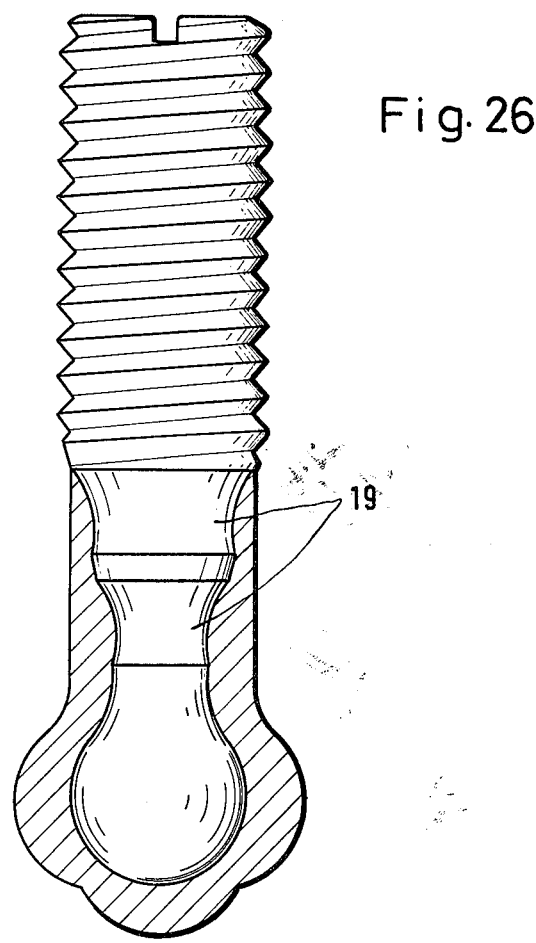

FIGS. 25 and 26 show in combination with an implant according to the example of FIGS. 1 to 4, an enhancement of the retention effect by means of one or two transverse grooves 19 in the area of the shaft. Said grooves may be provided additionally to the corresponding configurations of the thickened part (see the embodiments of FIGS. 8 to 24) or else—as shown—in combination with a spherical thickened part.

With the invention (which also may be used in the front and lateral areas of the upper jaw to retain a prosthesis, whereby significant depth retaining effects may be obtained) satisfactory retention of the prosthesis may be attained, in particular with severely atrophied jawbones, i.e., in cases wherein practically no other implantalogical possibilities are available (aside from the very expensive superiostal frame work implantation). Especially the good retention and the improved chewing action attainable by the invention, should be emphasized. Upper jaw implantation is even more feasible and is effected with greater ease, because the upper jawbone is much more porous (spongier) in its structure than the lower jawbone and the mucous membrane of the upper jaw is much thicker than that of the lower jaw.

Implants according to the invention may be made of gold, but also of another strong material that is rigid in practice, with the inert titanium and surgical stainless steels being particularly suitable, for example, the material available on the market under the trademark of "Vitallium 2000".

As mentioned hereinabove and as indicated by the description hereinafter of the drill according to the invention and of its manipulation, the time of the dentist involved and the outlay for the material required is relatively low for implants of this type.

The drills to be used according to the invention for the implantation have the same drill body 20, that is standardized and has a diameter of 2.35 mm; it fits into any dental angle piece.

Figure 27:
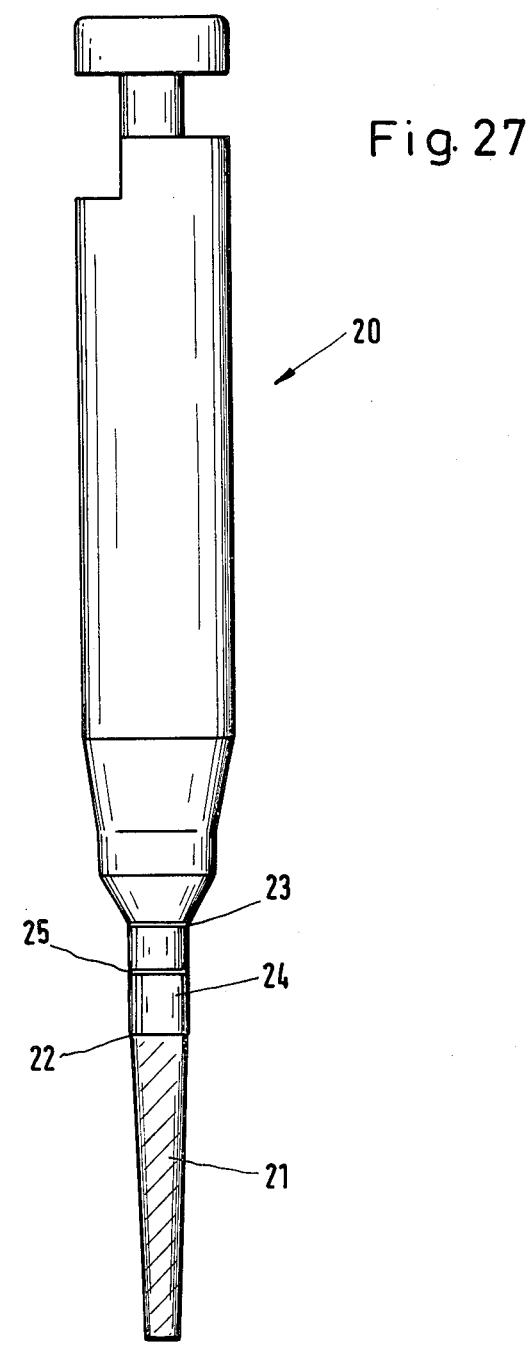
FIGS. 27 to 31 show possible embodiments of drills for the preparation of bone channels or openings to insert the implants according to the invention.

The first drill shown in FIG. 27 is a trepanning drill, with a working part 21 extending to a point 22, and having a length in the present example (for implants with the dimensions cited hereinabove as an example) to said point of 0.5 mm. This working part has at its tip a diameter of 5 mm and expands at the point 22 to a diameter of 1.0 mm. The cylindrical shaft part 24 between the point 22 and a first marking location 23 has a diameter of 1.0 mm and is 2 mm long. The parts 21 and 24 thus have an overall length of 7 mm. Trepanning is effected until the first marking 23 is located at the upper side of the jawbone or at the mucous membrane 4, respectively. A second marking 25 may be provided on the cylindrical shaft part 24; it shall be explained in more detail hereinafter.

Figure 28:
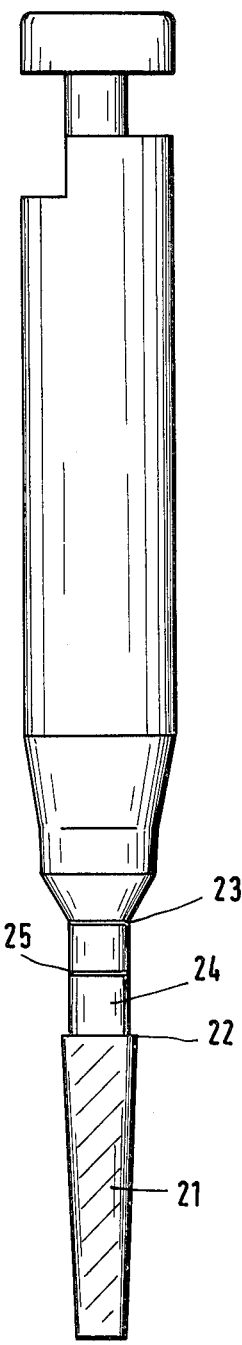
Figure 29:
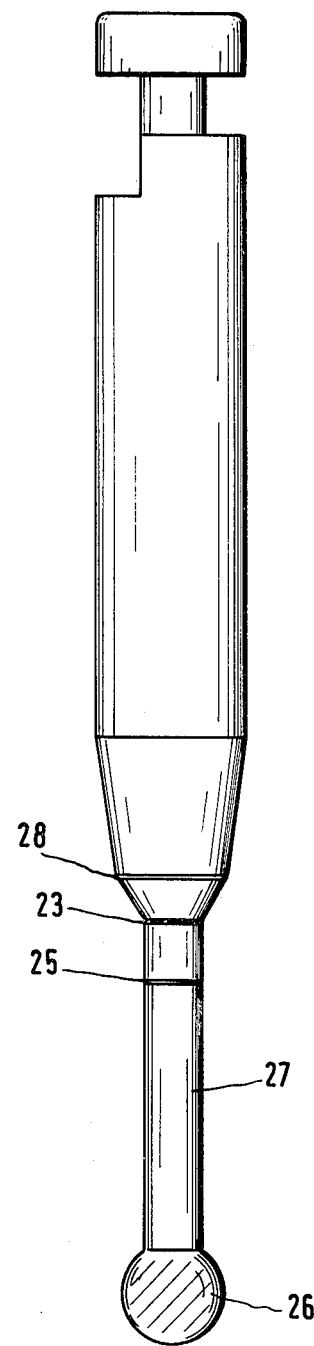

Subsequently, by means of a second drill (FIG. 28), having essentially the same dimensions as the first drill according to FIG. 27, the drilled opening is expanded. In FIG. 28 therefore the same reference numbers are used as in FIG. 25, with the exception that here the working part proper, with a length of 5 mm, has at its tip a diameter of 1.0 mm and expands to a diameter of 1.5 mm at the point 22, while the cylindrical drill shaft 25 has a diameter of 1.0 mm; it is therefore somewhat reduced in diameter in comparison with the working part itself. In this second drill, the working part and the shaft again are altogether 7 mm long. The channel 2 is hereby expanded, again to a depth of 7.0 mm of the implantation section of this numerical example, combined of parts 6 and 7, and 15 and 7, respectively. This is again attained, when the first marking 23 is located on the upper side of the bone, or at the mucous membrane 4, respectively.

After this work is continued with a third countersink drill (FIG. 29), to further expand the trepanned location. This drill equipped at its front end with a spherical cutter 26, having a diameter of 1.8 mm. The cylindrical shaft 27 connected with it has a diameter of 1.0 mm. The parts 26, 27 are also 7.0 mm long, altogether. This drill is again introduced to the first marking 23, as described hereinabove.

Figure 30:
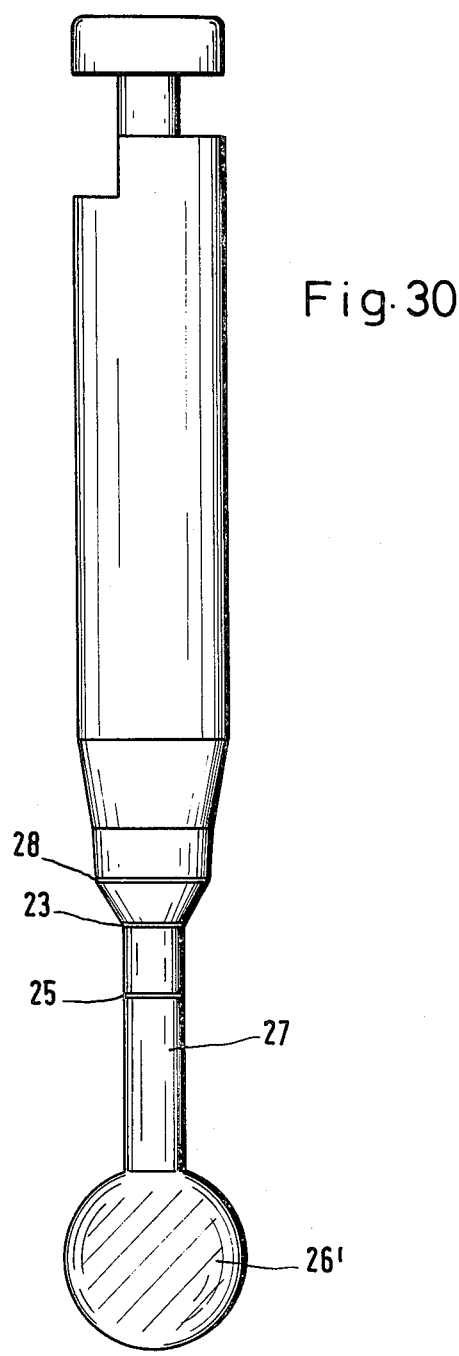
Figure 31:
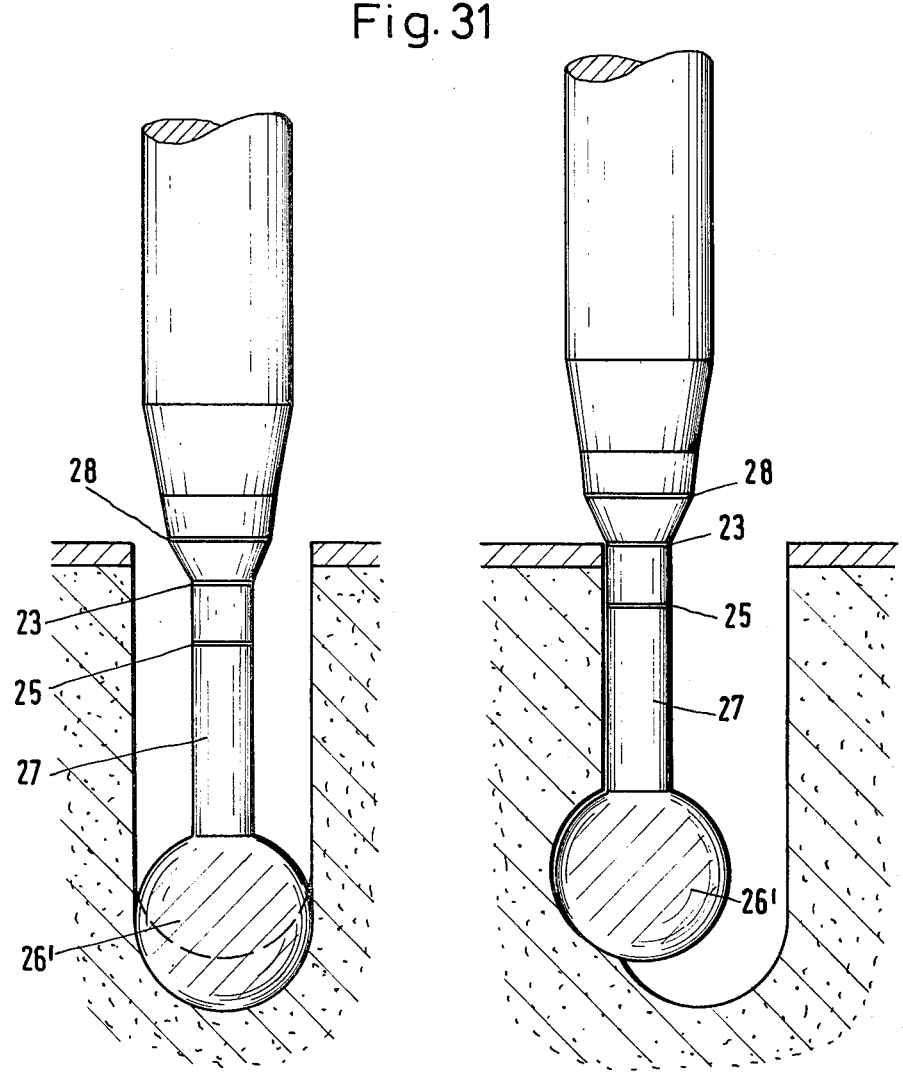

Subsequently, the existing trepanation in the spongy bone may be further expanded with a fourth drill, not shown, having a somewhat larger spherical cutter with a diameter of 2.3 mm, until finally the final diameter of the trepanned channel is established with the use of the drill shown in FIG. 30, with a spherical cutter 26' of a diameter of 3.1 mm. In order to maintain the depth corresponding to the implant, here again the total length of the spherical cutter 26' and the shaft 27 must be equal to the overall length of the thickened part 7 and the shaft 6 in the example of FIGS. 1 to 4, and of the thickened part 7 and the shaft 15 in the examples of FIGS. 5 and 6, respectively; it is 7 mm with the data cited therein. If, however, the trepanned channel is to be drilled for a shorter implant (for example, the form of embodiment of FIG. 5 may be shortened in its shaft part by 1 mm), drilling must be continued only until the second marking 25 is located in the range of the mucous membrane 4. The markings may consist of circumferential grooves or the like.

Let us, however, assume the abovecited depth of 7 mm. Then, the fifth drill must also be introduced to the first marking 23. Finally, this drill will be introduced additionally to a third marking 28, in order to produce an additional deepening of the drilled opening (FIG. 31a). The drill is then withdrawn to the marking 23 (or 25) and its shaft is applied against the channel, i.e., the wall of the jawbone already trepanned, while the drill moved along the inside of the channel on its circumference, i.e., in a circle, while maintaining its position in depth (FIG. 31b). The three-dimensional expansion of the undercut 3 of the trepanned channel within the jawbone is thereby effected at a standardized depth.

It therefore is important that all of the drills have an equal length to the marked location 23 (or 25). With all of the drills having a spherical cutter, the drill shaft 27 is cylindrical and smaller in diameter than the working part, i.e. the spherical cutter. This provides better vision during the drilling and, above all, the chips may be rinsed out easier.

If the drill markings 23 (or 25) are observed correctly, the expansion or undercut 3 is located exactly at the depth desired. As a result, the implant will be suspended following its insertion, including the thickened part, in the center of the bore without contacting the bone.

The drills according to the invention may also have a configuration so that they may be operated by means of a turbine drive customary in dental practice. The standardized drill body is then smaller and narrower.

I claim:

1. A retainer element for a dental prosthesis that is releasably insertable into an artificial recess having an undercut portion formed in a jawbone comprising:
    (a) a retainer body threadingly attachable to the dental prosthesis such that the longitudinal portion of the retainer body relative to the dental prosthesis may be adjusted by rotating the retainer body with respect to the dental prosthesis;
    (b) a conical shaft extending from a first end of the retainer body a length sufficient to enable the conical shaft to extend into the recess formed in the jawbone, the cross-sectional diameter of the conical shaft decreasing from its maximum value adjacent the retainer body in a direction away from the retainer body; and, (c) an enlarged, thickened head portion formed on the distal end of the conical shaft such that it may be located in the undercut portion of the artificial recess formed in the jawbone, the enlarged head portion having a maximum diametrical dimension measured in a plane extending generally perpendicular to a longitudinal axis of the retainer body no greater than the maximum diameter of the conical shaft.

2. The retainer element of claim 1 wherein the diameter of the enlarged head portion gradually increases from its initial point of contact with the conical shaft to its maximum value.

3. The retainer element of claim 1 wherein a second end of the retainer body defines a recess for engagement with a tool to effect rotation of the retainer element.

4. The retainer of claim 1 wherein the enlarged, thickened head portion is generally sperical in shape.

5. The retainer of claim 1 wherein the enlarged, thickened head portion is in the form of a rotational ellipsoid, the longitudinal axis of said ellipsoid coinciding with the longitudinal axis of the retainer body.

6. The retainer element of claim 1 wherein the enlarged, thickened head portion is egg-shaped, the longitudinal axis of the egg coinciding with the longitudinal axis of the retainer body and the tip of the egg facing away from the threaded body portion of the retainer element.

7. The retainer element of claim 1 wherein an upper portion of the enlarged, thickened head portion facing the retainer body is concavely curved in a direction extending away from the retainer body.

8. The retainer element of claim 1 wherein the enlarged, thickened head portion has at least one horizontal groove about its periphery.

9. The retainer element of claim 1 wherein the enlarged, thickened head portion has at least one vertical groove or recess.

10. The retainer element of claim 1 wherein the enlarged, thickened head portion has at least one shoulder adjacent, but disposed at an angle to its equator.

11. The retainer element of claim 1 wherein the conical shaft connecting the enlarged, thickened head portion to the retainer body has at least one circumferential groove.

12. A dental prosthesis attachable to the jawbone of a user comprising:

(a) a prosthesis device defining at least one threaded opening facing in a direction toward a jawbone when the device is worn by an individual;

(b) a retainer body threadingly attached in the threaded opening of the dental prosthesis such that its longitudinal position with respect to the dental prosthesis may be adjusted by rotating the retainer body with respect to the dental prosthesis;

(c) a conical shaft extending from the retainer body in a direction away from the dental prosthesis device a length sufficient to enable the conical shaft to extend into an artificial recess formed in the jawbone, the cross-sectional diameter of the conical shaft decreasing from its maximum value adjacent to the retainer body in a direction away from the prosthesis; and, (d) an enlarged, thickened head portion formed on the distal end of the conical shaft such that it extends into an undercut portion of the artificial recess formed in the jawbone, the enlarged head portion having a maximum diameter measured in a plane extending generally perpendicular to a longitudinal axis of the retainer body no greater than the maximum diameter of the conical shaft.

13. The dental prosthesis of claim 12 wherein the dental prosthesis device defines a plurality of threaded openings and the longitudinal axis of at least one threaded opening is oriented obliquely with respect to a vertical axis of the prosthesis.

14. A method of attaching a dental prosthesis to a jawbone of a user comprising the steps of:

(a) forming at least one threaded opening in the dental prosthesis;

(b) drilling a conical opening through the mucous membrane surrounding the jawbone and into the jawbone;

(c) expanding the diameter of the first conical opening by passing a drill having a first spherical cutting surface down through the conical opening;

(d) expanding the diameter of the opening in the jawbone and forming an undercut portion near the end of the opening;

(e) threadingly attaching at least one retainer element to the dental prosthesis such that a conical shaft with an enlarged head portion formed on its end extends from the threaded portion of the retainer element, the maximum diameter of the enlarged head portion being no greater than the maximum diameter of the conical shaft; and, (f) placing the dental prosthesis on the user such that the enlarged head portion extends into the undercut portion of the opening in the jawbone.

15. The method according to claim 14 comprising the additional step of expanding the conical opening by passing therethrough a second conical drill prior to expanding the opening with the drill having a spherical cutting surface.

* * * * *